United States Patent [19]

Murphy et al.

[11] Patent Number: 5,614,179
[45] Date of Patent: *Mar. 25, 1997

[54] COSMETIC DEODORANT PRODUCTS CONTAINING A POLYMER/FRAGRANCE-ENCAPSULATED BICARBONATE INGREDIENT

[75] Inventors: Richard T. Murphy, Belle Mead; Wolfgang R. Bergmann, Princeton, both of N.J.

[73] Assignee: Church & Dwight Co., Inc., Princeton, N.J.

[ * ] Notice: The term of this patent shall not extend beyond the expiration date of Pat. No. 5,585,093.

[21] Appl. No.: 534,845
[22] Filed: Sep. 27, 1995
[51] Int. Cl.⁶ .............................. A61K 7/32; A61K 9/32
[52] U.S. Cl. .......................... 424/65; 424/490; 424/717
[58] Field of Search .......................... 424/717, 65, 490

[56] References Cited

U.S. PATENT DOCUMENTS

| | | | |
|---|---|---|---|
| 3,198,251 | 8/1965 | Shore | 424/717 |
| 4,919,934 | 4/1990 | Deckner et al. | 424/401 |
| 5,376,372 | 12/1994 | Murphy et al. | 424/66 |
| 5,411,750 | 5/1995 | Lajoie et al. | 424/717 |
| 5,424,270 | 6/1995 | Winston | 514/772.3 |

*Primary Examiner*—Peter F. Kulkosky
*Attorney, Agent, or Firm*—Irving M. Fishman

[57] ABSTRACT

This invention provides deodorant and antiperspirant-deodorant cosmetic stick and roll-on products with an organic matrix having a dispersed particle phase of an encapsulated bicarbonate salt ingredient such as sodium bicarbonate. The particle surfaces are coated with a film-forming medium comprising a blend of a polymer and a fragrance ingredient. When this type of cosmetic product is applied to underarm surfaces, the deodorizing activity is signaled by the release of a fragrance aroma.

45 Claims, No Drawings

COSMETIC DEODORANT PRODUCTS CONTAINING A POLYMER/FRAGRANCE-ENCAPSULATED BICARBONATE INGREDIENT

CROSS-REFERENCE TO RELATED APPLICATIONS

The subject matter of this patent application is related to that described in patent application Ser. No. 08/354,235, filed Dec. 9, 1994 abandoned; and copending patent application Ser. No. 08/437,022, filed May 8, 1995; incorporated by reference.

BACKGROUND OF THE INVENTION

Alkali metal bicarbonate is a commodity reagent which has found application in a broad variety of products such as laundry detergents, deodorizers, creams and lotions, dentifrices, antacids, buffers, fungicides, and the like.

The inclusion of particulate alkali metal bicarbonate in a cosmetic deodorant stick or roll-on formulation provides a product with improved deodorant properties. Dimensional instability of a cosmetic stick or roll-on product containing bicarbonate ingredient, and the esthetic appearance and the "feel" on the skin, are among the difficulties encountered in the preparation of a low residue cosmetic antiperspirant-deodorant product. The high density of a suspended particle-phase of bicarbonate ingredient relative to the low density of an organic matrix phase contributes to the instability and settling of the bicarbonate particle phase in a cosmetic stick or roll-on personal care product.

In addition, a bicarbonate ingredient often is incompatible with the active astringent salts and with other ingredients of conventional cosmetic stick products. A bicarbonate ingredient in direct contact with acidic ingredients is susceptible to decomposition into carbon dioxide and water.

An additional factor is the risk of a fragrance ingredient incompatibility with bicarbonate and astringent ingredients.

There is continuing interest in the development of reagents such as alkali metal bicarbonate and ammonium bicarbonate which have a uniform fine grain particle size, and exhibit a novel combination of properties when utilized as an ingredient in personal care, biologically active, household, and specialty type products. There is also interest in the development of a bicarbonate powder which is in a form that is stable when blended with an acidic ingredient in a formulation.

Accordingly, it is an object of this invention to provide an alkali metal bicarbonate or ammonium bicarbonate powder which has a fine grain particle size, and which is free-flowing and essentially free of agglomerated solids.

It is another object of this invention to provide an encapsulated powder composition of particles which are composed of polymer/fragrance-coated crystallites of bicarbonate salt, and which have a lower density than the inner core bicarbonate crystallites of the encapsulated particles.

It is another object of this invention to provide a cosmetic deodorant product which has a content of an encapsulated liquid fragrance ingredient with controlled release properties.

It is a further object of this invention to provide a cosmetic deodorant product which, when applied to underarm surfaces, signals deodorizing activity by the release of a fragrance aroma.

Other objects and advantages of the present invention shall become apparent from the accompanying description and examples.

DESCRIPTION OF THE INVENTION

One or more objects of the present invention are accomplished by the provision of an encapsulated bicarbonate salt powder composition comprising discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

The bicarbonate salt crystallites can have an average particle size between about 5–150 microns. A preferred range for the bicarbonate crystallites is an average particle size between about 5–80 microns. A present invention encapsulated powder composition typically is free-flowing and essentially free of agglomerated solids.

The term "discrete" as employed herein refers to crystallites which are individually distinct solids.

The term "average particle size" as employed herein refers to the average of the largest dimension of particles.

The particulate bicarbonate salt starting material of an invention encapsulated powder composition is selected from alkali metal and ammonium bicarbonates, such as sodium bicarbonate, potassium bicarbonate and ammonium bicarbonate, and any mixtures thereof.

The fragrance starting material can be selected from normally solid organic compounds which include vanillin, ethylvanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, proeugenol acetate, evernyl, and the like. Other suitable fragrances such as menthol and camphor exhibit kinesthetic properties, and are utilized in personal products to provide a "cool feel" on skin surfaces.

The fragrance starting material also can be selected from normally liquid organic compounds, which typically comprises one or more volatile organic compounds which are available from perfumery suppliers such as Firmenich Inc., Takasago Inc. Noville Inc., Quest Co., and Givaudan-Roure Corp.

Most conventional fragrance materials are volatile essential oils. The fragrance can be a synthetically formed material, or a naturally derived oil such as oil of Bergamot, Bitter Orange, Lemon, Mandarin, Caraway, Cedar Leaf, Clove Leaf, Cedar Wood, Geranium, Lavender, Orange, Origanum, Petitgrain, White Cedar, Patchouli, Lavandin, Neroli, Rose absolute, and the like.

A wide variety of chemicals are known for perfumery, such as aldehydes, ketones, esters, alcohols, terpenes, and the like. A fragrance can be relatively simple in composition, or can be a complex mixture of natural and synthetic chemical components.

A typical scented oil can comprise woody/earthy bases containing exotic constituents such as sandalwood oil, civet, patchouli oil, and the like. A scented oil can have a light floral fragrance, such as rose extract or violet extract. Scented oil also can be formulated to provide desirable fruity odors, such as lime, lemon or orange.

Synthetic types of fragrance compositions either alone or in combination with natural oils are described in U.S. Pat.

Nos. 4,314,915; 4,411,829; and 4,434,306; incorporated herein by reference. Other artificial liquid fragrances include geraniol, geranyl acetate, eugenol, isoeugenol, linalool, linalyl acetate, phenethyl alcohol, methyl ethyl ketone, methylionone, isobornyl acetate, and the like.

The application of the polymer/fragrance coating medium to the bicarbonate crystallite surfaces is accomplished by conventional means such as pan coating, fluidized coating, centrifugal fluidized coating, and the like. The coating polymer and fragrance usually are dissolved in a suitable solvent such as water, methanol, ethanol, acetone, tetrahydrofuran, ethyl acetate, dimethylformamide, and the like, as appropriate for the selected polymer and fragrance species. A polymer/fragrance coating medium also can be applied in the form of an emulsion or suspension. After the coating medium is applied to the crystallites, the solvent medium is removed by evaporation, thereby forming a continuous film coating which encapsulates the discrete fine grain crystallites.

In a preferred coating procedure, bicarbonate powder is dispersed in an aqueous medium which contains a coating medium emulsion. The emulsified aqueous dispersion is atomized and sprayed into heated air to remove the aqueous phase, and to provide a free-flowing polymer/fragrance-encapsulated bicarbonate powder product.

The coating thickness on the crystallite surfaces typically will vary in the range between about 0.1–20 microns. The polymer/fragrance coating can constitute between about 5–70 weight percent of the total dry weight of the coated crystallites.

In a further procedure, the coated bicarbonate particles can be modified by the application of a second coating of a film-forming polymer which is the same or different than the polymer constituent of the first coating medium and which does not contain a fragrance ingredient. The multiple surface coatings on the particles can comprise between about 10–75 weight percent of the dry particle weight.

A polymer employed for coating the bicarbonate and fragrance crystallites is selected from hydrophilic organic polymers and hydrophobic (water-insoluble) organic polymers and mixtures thereof.

A hydrophilic polymer employed for coating the ingredient crystallites is selected from water-soluble and water-dispersible organic polymers. A mixture of polymers can be employed, and a content of between about 0.5–60 weight percent of a water-insoluble polymer, based on the polymer weight, can be included with a hydrophilic polymer.

The term "hydrophilic" as employed herein refers to an organic polymer which has a water-solubility of at least about one gram per 100 grams of water at 25° C. The term "hydrophobic" or "water-insoluble" as employed herein refers to an organic polymer which has a water solubility of less than about one gram per 100 grams of water at 25° C.

Suitable hydrophilic polymers for coating bicarbonate crystallites include gum arabic, gum karaya, gum tragacanth, guar gum, locust bean gum, xanthan gum, carrageenan, alginate salt, casein, dextran, pectin, agar, sorbitol, 2-hyroxyethyl starch, 2-aminoethyl starch, maltodextrin, amylodextrin, 2-hydroxyethyl cellulose, methyl cellulose, carboxymethyl cellulose salt, cellulose sulfate salt, polyvinylpyrrolidone, polyethylene glycol, polypropylene glycol, polyethylene oxide, polyvinyl alcohol/acetate, polyacrylamide, and the like. Polyvinyl acetate is illustrative of a water-insoluble polymer which can be included as an additional coating component to moderate the hydrophilicity of a hydrophilic polymer coating.

Suitable water-insoluble polymers, alone or in combination with one or more other components, for coating ingredient crystallites include polyvinyl acetate, polyacrylamide, polyvinyl chloride, polystyrene, polyethylene, polyurethane, and the like.

For purposes of release of the core matrix bicarbonate salt ingredient and coating fragrance ingredient in the encapsulated particles when introduced into an aqueous environment, a surface coating with a water-insoluble polymer preferably has a content between about 5–30 weight percent of a particulate water-extractable organic or inorganic filler, such as sodium bicarbonate, sodium carbonate, sodium chloride, calcium chloride, monosaccharide or disaccharide, sorbitol, mannitol, and the like.

The rate of release of core matrix bicarbonate salt and coating fragrance content of the particles under moisture conditions can be controlled by the quantity and type of film-forming polymer on the particle surfaces.

Low molecular weight hydrophilic polymers will release the particle bicarbonate and fragrance ingredients at a relatively fast rate in the presence of moisture. High molecular weight polymers which are less hydrophilic will release at a relatively slow rate. Additional rate control is obtained by employing mixtures of polymer components of varied hydrophilicity.

Polyethylene glycol (M.W. of 4000) or polyvinyl alcohol will release the particle bicarbonate and fragrance content at a relatively fast rate. Polyethylene oxide (M.W. of 4,000,000) or partially hydrolyzed polyvinyl acetate will release at a relatively slow rate. Polyvinylpyrrolidone will release the particle bicarbonate and fragrance content at an intermediate rate when in contact with underarm type of moisture.

In another embodiment this invention provides a cosmetic deodorant product comprising a liquid, semi-solid or solid organic matrix which contains between about 0.5–20 weight percent, based on the product weight, of an encapsulated powder composition homogeneously dispersed therein, wherein the encapsulated powder composition comprises discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

A present invention cosmetic stick or roll-on deodorant product can contain between about 5–25 weight percent of an antiperspirant compound as an additional ingredient.

A present invention cosmetic stick product can consist of a solid organic matrix comprising the following parts by weight of ingredients:

| | |
|---|---|
| volatile oil | 10–55 |
| liquid emollient | 1–35 |
| low melting point wax | 12–30 |

The solid organic matrix has homogeneously dispersed therein between about 0.5–20 weight percent, based on the product weight, of an encapsulated powder composition as described hereinabove.

An invention antiperspirant-deodorant cosmetic stick product typically contains the following weight proportions of main ingredients:

| Ingredient | Weight |
| --- | --- |
| volatile oil | 25–50 |
| liquid emollient | 2–20 |
| wax (MP 95°–180° F.) | 15–20 |
| antiperspirant | 20–28 |
| encapsulated bicarbonate/ fragrance powder | 0.1–25 |
| surfactant | 1–3 |

The volatile oil ingredient preferably is selected from silicone and branched-chain hydrocarbon compounds.

A volatile silicone oil ingredient in a cosmetic stick or roll-on product of the present invention preferably is a cyclic or linear polydimethylsiloxane containing between about 3–9 silicon atoms. A suitable cyclic volatile polydimethylsiloxane compound is illustrated by the formula:

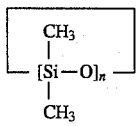

where n is an integer with a value of about 3–7.

A suitable linear polydimethylsiloxane is illustrated by the formula:

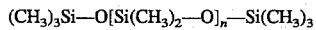

where n is an integer with a value of about 1–7.

Linear volatile silicone compounds generally have viscosities of less than about 5 centistokes at 25° C., while the cyclic type compounds have viscosities of less than about 10 centistokes.

Typical of the volatile silicone compounds that can be employed for purposes of the present invention is cyclomethicone, which is a cyclic dimethylpolysiloxane conforming to the above formula where n averages between 3–6. Dow Corning 245 Fluid (Dow Corning) is a cyclic volatile silicone which is commercially available. *CTFA Cosmetic Ingredient Dictionary,* Third Edition, (Estrin et al., Editors; The Cosmetic, Toiletry and Fragrance Association, Inc.; 1982) lists cyclic silicones on page 60, under the entry "Cyclomethicone".

A volatile hydrocarbon oil type of ingredient preferably is a $C_{12}$–$C_{20}$ branched-chain hydrocarbon compound or mixture. Suitable volatile branched-chain hydrocarbon oils include isododecane ($C_{12}$), isohexadecane ($C_{16}$), isoeicosane ($C_{20}$), and the like. These types of branched-chain hydrocarbons are marketed by Permethyl Corporation under tradenames such as Permethyl 99A, Permethyl 101A and Permethyl 102A.

The liquid emollient ingredient of an invention cosmetic stick or roll-on product is selected from one or more water-insoluble organic compounds which are liquid at 25° C. and which contribute a combination of properties that are advantageous in an invention cosmetic stick or roll-on product.

The term "water-insoluble" as employed herein refers to an emollient ingredient which has a water-solubility of less than about one gram per 100 grams of water at 25° C.

A present invention emollient ingredient exhibits a low degree of irritation and toxicity in topical applications, and provides a softening or soothing effect on surface skin tissue.

Preferred water-insoluble liquid emollients include fatty acids such as oleic and ricinoleic; fatty alcohols such as oleyl, lauryl and hexadecyl; esters such as diisopropyl adipate, benzoic acid esters of $C_9$–$C_{15}$ alcohols, and isononyl isononanoate; alkanes such as mineral oil; silicones such as dimethylpolysiloxane and cyclic dimethylpolysiloxane; and ethers such as polyoxypropylene butyl ether and polyoxypropylene cetyl ether. Preferred water-insoluble liquid emollients include diisopropyl adipate, 2-ethylhexyl palmitate, dimethylpolysiloxane (50 cst.), and polyoxypropylene (14) butyl ether.

The low melting point wax ingredient of a present invention cosmetic stick product comprises one or more organic compounds which have a melting point in the range between about 95°–180° F.

Suitable types of wax-like compounds include fatty acids, fatty alcohols, fatty acid esters, fatty acid amides, and the like, which have an aliphatic chain length between about 8–30 carbon atoms. Illustrative of wax-like compounds are cetyl alcohol, palmitic acid, myristyl alcohol, stearyl alcohol, paraffin, and the like, and mixtures thereof.

The low melting point wax ingredient can include up to about 30 weight percent, based on the weight of wax ingredient, of a wax which has a melting point between about 180°–220°F. Illustrative of these higher melting waxes are beeswax, spermaceti, carnauba, bayberry, candelilla, montan, ozokerite, ceresin, paraffin, castor wax, Fischer-Tropsch waxes, and the like.

The antiperspirant ingredient of a present invention cosmetic stick or roll-on product typically is a particulate astringent compound which has an average particle size between about 1–100 microns. Superior cosmetic stick properties are obtained if part or all of the antiperspirant ingredient is in the form of particles which have a diameter less than about one micron. Optionally, the antiperspirant ingredient can be pre-coated with a polymer to prevent interaction with the other ingredients, and to provide a sustained-release antiperspirant activity under application conditions.

Suitable astringent compounds include aluminum chloride, aluminum chlorohydrate, aluminum sulfocarbolate, aluminum sulfate, aluminum-zirconium chlorohydrate, zinc sulfate, zinc sulfocarbolate, and zirconium chlorohydrate. Preferred types of astringent compounds are aluminum chlorohydrates and aluminum-zirconium chlorohydrates, such as aluminum-zirconium trichlorohydrex glycine. Aluminum-zirconium tetrachlorohydrex glycine is commercially available as Rezal 36 GP Superultrafine (Reheis), and Reach AZP 908 (Reheis).

Optional ingredients also may be included in an invention cosmetic formulation, such as bacteriostats, fungistats, fillers, stabilizing agents, antioxidants, pigments, coloring agents, perfumes, chelating agents, and the like.

A surfactant ingredient of an invention cosmetic formulation is selected from nonionic, cationic and anionic polymers. Suitable surfactant polymers include cetyltrimethylammonium bromide; sodium lauryl sulfate; sodium dodecylbenzenesulfonate; ammonium lignosulfonate; condensation products of ethylene oxide with fatty alcohols, amines or alkylphenols; partial esters of fatty acids and hexitol anhydrides; polyalkylene glycol esters; and the like. Illustrative of a preferred type of surfactant polymer is polyethylene glycol (PEG) stearate, which is commercially available as PEG 600 distearate.

A bacteriostat such as 2,4,4'-trichloro-2'-hydroxydiphenyl ether (Triclosan) typically is added in a quantity between about 0.08–3 weight percent, based on the weight of the cosmetic stick or roll-on product.

In another embodiment this invention provides a cosmetic roll-on product consisting of a liquid organic matrix comprising the following parts by weight of ingredients:

| Volatile oil | 55–70 |
|---|---|
| liquid emollient | 3–10 | and the liquid organic matrix has homogeneously dispersed therein about 0.5–20 parts by weight, based on the product weight, of an encapsulated powder composition comprising discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

In another embodiment this invention provides a method of practicing personal hygiene which comprises applying a present invention cosmetic stick or roll-on product to underarm surfaces in a deodorant-effective amount, wherein the initiation and continuation of deodorizing activity is signaled by an organoleptic fragrance aroma.

A significant advantage of the present invention cosmetic formulation is the signaling of deodorizing activity by a sensible aroma of fragrance which is released after underarm application of the cosmetic formulation. After application, underarm moisture initiates a continuous release of bicarbonate salt deodorant and fragrance from the polymer/fragrance-coated particles of encapsulated bicarbonate salt core matrix.

Other advantages are provided by the practice of the present invention. As noted in the Background section of the specification, the relative densities of the liquid and solid phases in a cosmetic stick or roll-on product directly affects the stability and esthetics of the formulations.

Density matching of inorganic and organic phases is a significant factor in cosmetic stick and roll-on products. The present invention formulations contain a dispersed phase of polymer/fragrance-coated bicarbonate deodorant particles of lower density which more closely matches the density of the organic matrix of a cosmetic stick or roll-on product than does uncoated bicarbonate ingredient.

When there is density matching of organic matrix and dispersed encapsulated bicarbonate particle phases, a cosmetic stick or roll-on product has improved dimensional stability, and better esthetic appearance and "feel" when applied to human skin.

In general, the ingredients of a cosmetic formulation can be blended in any order. However, in the practice of the invention process for cosmetic stick manufacture there is advantage in utilizing a phased order of ingredient addition and blending under controlled temperature conditions. Additional advantage is obtained in the invention process if there is a minimal time lapse between the encapsulated alkali metal bicarbonate deodorant ingredient addition step and the cosmetic stick container filling and solidifying step. Alkali metal bicarbonate can convert to alkali metal carbonate, carbon dioxide and water at elevated temperatures.

Adding the encapsulated bicarbonate salt as the last ingredient of the blended formulation, and processing the formulation to the solid cosmetic stick formation stage within a short time period, are factors which minimize the degradation of the bicarbonate salt ingredient, and the undesirable formation of water and carbon dioxide vapor byproducts. The addition and mixing of the bicarbonate salt ingredient into the formulation, and the dispensing of the formulation into cosmetic stick containers, can be accomplished as an essentially instantaneous procedure by utilizing an integrated mixing valve nozzle device, such as the type described in U.S. Pat. Nos. 2,816,518; 3,454,198; 3,949,904; 4,318,429; 4,549,813; 5,046,538; 5,094,276; and the like.

The practice of the invention process for the production of a cosmetic stick product can be conducted in conventional equipment, and is readily adaptable to a commercial-scale manufacturing operation.

The hardness of a present invention cosmetic stick can have a value which varies in the range between about 2.0–8.0, and preferably is in the range between about 2.3–3.3.

The penetration values (in millimeters) of the cosmetic stick products described herein are measured with a Universal Penetrometer, Model TS-73510 AN-2 (Precision Scientific Inc.).

The penetration values are obtained by following a standardized procedure in accordance with ASTM Method D217-94.

A present invention antiperspirant-deodorant cosmetic stick or roll-on product has exceptional properties for treating or preventing perspiration and malodor associated with human underarm perspiration. A present invention cosmetic formulation can be applied effectively with safety and comfort for reduction of underarm perspiration and offensive odors.

The following Examples are further illustrative of the present invention. The components and specific ingredients are presented as being typical and various modifications can be derived in view of the foregoing disclosure within the scope of the invention.

EXAMPLE I

This Example illustrates a fluidized bed procedure for coating particulate bicarbonate with a film-forming hydrophilic polymer/fragrance medium in accordance with the present invention.

A fluidized bed vessel is utilized which is equipped with a Wurster air-suspension coater system (WARF) as described in U.S. Pat. No. 4,568,559 and U.S. Pat. No. 4,877,621.

A coating solution is prepared by dissolving polyethylene glycol (60 g, Poly-G 2000, Olin Corp.) and cedrol (8 g) in ethanol (60 g).

Sodium bicarbonate is utilized as the core matrix crystallites. The sodium bicarbonate (Particle Size Technology, Inc.) has an average particle size of about 5 microns, and 90 percent of the particles have a diameter less than 20 microns.

The sodium bicarbonate powder is charged into the coating chamber.

Compressed air is introduced into the coating chamber, and the polymer/fragrance coating solution is sprayed on the air-suspended bicarbonate crystallites, until the coating weight is about 30% of the total dry weight of the coated particles.

The procedure is repeated, except that hydroxypropylmethylcellulose (Methocel 60 HG, Dow Chemical Co.) is employed as the hydrophilic polymer.

The procedure is repeated, except that maltodextrin (Lodex 10; Durkee Foods) or amylodextrin is employed as the water-soluble polymer, and 0.5 g of a surfactant is included in the solution (polyoxyethylenesorbitan monolaurate; Tween 20; ICI Americas, Inc.).

The procedure is repeated except that an 80/20 by weight mixture of polyvinylpyrrolidone/polyvinyl acetate is employed as the crystallite-coating polymer ingredient.

In a separate procedure, initially coated particles are re-coated with the polyethylene glycol in ethanol solution, except that no fragrance is included in the second coating solution. Each of the first and second coatings on the particles is about 15 weight percent of the total dry weight of the coated particles.

EXAMPLE II

This Example illustrates a procedure for the preparation of an antiperspirant-deodorant cosmetic stick product in accordance with the present invention.

A stainless steel tank is provided which is equipped with turbine agitation.

Silicone oil DC 245 (400 lbs, Dow Corning) and Dow DC 200 (37.50 lbs, Dow Corning) are charged to the mixing tank. Agitation (55–65 RPM) is initiated, and heating the liquid medium to 176° F. is commenced.

During the heating period, the following ingredients are added to the stirred liquid medium:

|  | lbs. |
|---|---|
| Lanette 18 DEO[(1)] | 175.00 |
| Castorwax MP-80[(2)] | 31.25 |
| ICI G-2162[(3)] | 6.25 |

[(1)]Stearyl alcohol; Henkel.
[(2)]Hydrogenated castor oil; RTD.
[(3)]PEG 25 PG stearate; ICI.

The mixture is stirred at 176° F. for about 30 minutes until the ingredients are melted and the liquid medium is homogeneous. The stirring speed is reduced to about 35 RPM, then Cyprus Supra A Talc 1625 (18.75 lbs, Cyprus) and Reach AZP 908 aluminum-zirconium tetrachlorohydrex glycine (312.50 lbs, Reheis) are added. The temperature is maintained at 176° F. for about 40 minutes until the fluid medium is uniform, and then the temperature is lowered to 154° F.

A polymer/fragrance-coated sodium bicarbonate powder (148 lbs.) is added with stirring to Silicone oil DC 245 (200 lbs, Dow Corning) in a second mixing tank at a temperature of 154° F. to form a homogeneous suspension medium. The sodium bicarbonate crystallites are pre-coated with a coating of amylodextrin/2 weight percent maple lactone (Firmenich) employing a fluidized bed type procedure as described in Example I.

The contents of the two mixing tanks which contain heated fluid medium are transferred to separate fill tanks through a Greer mill, and the fill tanks are connected to a mixing and dispensing nozzle device, of the type described in U.S. Pat. No. 5,094,276. The nozzle device is adapted for homogeneously blending the two separate streams of fluid media, and dispensing a predetermined quantity of the blended fluid.

Plastek 2 oz. bottom-fill stick containers are filled with the blended fluid. The container contents are cooled to a room temperature solid stick over a period of about 45 minutes. The average hardness value of the solid sticks is 2.8 millimeters (ASTM D217-94).

EXAMPLE III

This Example illustrates a precipitation procedure for forming crystallites of potassium bicarbonate, and coating the bicarbonate crystallites with a hydrophilic polymer/fragrance medium in accordance with the present invention.

A coating solution is prepared by dissolving polyethylene glycol (10 g, Poly-G 2000, Olin Corp.), propylene glycol butyl ether (5 g, PPG 14, Americol), polyoxyethylenesorbitan monolaurate (1.0 g; Tween 20; ICI Americas, Inc.), and Coumarin (2 g) in 1-propanol (325 g).

A solution of potassium bicarbonate (35 g) in water (125 g) is prepared. The suspension medium then is added dropwise to the coating solution with high speed stirring.

The admixture which forms is a suspension of potassium bicarbonate crystallites in the liquid medium. The liquid medium is concentrated to dryness by removal of water/1-propanol azeotrope under vacuum at 60° C. in a rotating evaporator.

The resultant dry powder is composed of particles which consist of a 33% by weight coating on an inner core of single and multiple crystallites of potassium bicarbonate. The potassium bicarbonate crystallites have particle size distribution substantially in the range of 1–30 microns.

EXAMPLE IV

This Example illustrates the preparation of an antiperspirant-deodorant roll-on product in accordance with the present invention.

A roll-on formulation is prepared by blending the following proportions of ingredients:

|  | lbs. |
|---|---|
| Silicone oil DC 245 | 60.90 |
| Quaternium-18 hectorite clay (Rheox) | 9.50 |
| Reach AZP 908 | 23.00 |
| Encapsulated potassium bicarbonate[(1)] | 6.00 |
| Cab-o-Sil fumed silica (Cabot) | 0.60 |
| Propylene carbonate | 0.50 |

[(1)]Prepared by an Example I type of fluidized bed procedure. Potassium bicarbonate powder is encapsulated with a coating of amylodextrin/10 weight percent ethylvanillin.

The roll-on formulation exhibits excellent dimensional stability when packaged and maintained under storage conditions for six months.

What is claimed is:

1. A cosmetic deodorant product comprising an organic matrix which contains between about 0.5–20 weight percent of an encapsulated powder composition homogeneously dispersed therein, wherein the encapsulated powder composition comprises discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

2. A cosmetic deodorant product in accordance with claim 1 which is a cosmetic stick or roll-on formulation.

3. A cosmetic stick product consisting of a solid organic matrix comprising the following parts by weight of ingredients:

| volatile oil | 10–55 |
|---|---|
| liquid emollient | 1–35 |
| low melting point wax | 12–30 | and the solid organic matrix contains between about 0.5–20 weight percent of an encapsulated powder composition homogeneously dispersed therein, wherein the encapsulated powder composition comprises discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

4. A cosmetic stick product in accordance with claim 3 wherein the volatile oil ingredient comprises a cyclic or linear polydimethylsiloxane containing 3–9 silicon atoms.

5. A cosmetic stick product in accordance with claim 3 wherein the volatile oil ingredient comprises a $C_{12}$–$C_{20}$ branched-chain hydrocarbon.

6. A cosmetic stick product in accordance with claim 3 wherein the liquid emollient ingredient is a water-insoluble organic acid, ester or ether compound.

7. A cosmetic stick product in accordance with claim 3 wherein the wax ingredient is selected from $C_8$–$C_{30}$ alcohol, acid, ester and amide compounds.

8. A cosmetic stick product in accordance with claim 3 wherein the encapsulated bicarbonate crystallites are sodium, potassium or ammonium bicarbonate or any mixture thereof.

9. A cosmetic stick product in accordance with claim 3 wherein the fragrance ingredient in the coating is a normally solid organic compound selected from vanillin, ethylvanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, isoeugenol acetate and evernyl, and mixtures thereof.

10. A cosmetic stick product in accordance with claim 3 wherein the fragrance ingredient in the coating is a normally liquid organic compound selected from natural or synthetic essential oils, geraniol, eugenol, linalool, citronellol, phenethyl alcohol, methyl ethyl ketone, methylionone and isobornyl acetate, and mixtures thereof.

11. A cosmetic stick product in accordance with claim 3 wherein the surface coating on the particles comprises between about 5–70 weight percent of the dry particle weight.

12. A cosmetic stick product in accordance with claim 3 wherein the polymer constituent of the surface coating on the particles is a hydrophilic polymer or a water-insoluble polymer or a mixture thereof.

13. A cosmetic stick product in accordance with claim 3 wherein the polymer constituent of the surface coating on the particles is a polysaccharidic derivative.

14. A cosmetic stick product in accordance with claim 3 wherein the polymer constituent of the surface coating on the particles is a hydrocolloid.

15. A cosmetic stick product in accordance with claim 3 wherein the polymer constituent of the surface coating on the particles is a starch derivative.

16. A cosmetic stick product in accordance with claim 3 wherein the polymer constituent of the surface coating on the particles is maltodextrin or amylodextrin or a mixture thereof.

17. A cosmetic stick product in accordance with claim 3 wherein the polymer constituent of the surface coating on the particles is a hydrophilic polymer having a content between about 0.5–40 weight percent of a water-insoluble polymer, based on the polymer weight.

18. A cosmetic stick product in accordance with claim 3 wherein the polymer constituent of the surface coating on the particles is a water-insoluble polymer having a content between about 5–30 weight percent of a particulate water-soluble organic or inorganic filler, based on the polymer weight.

19. A cosmetic stick product in accordance with claim 3 wherein the surface-coated particles have a second coating of a film-forming polymer which is the same or different than the polymer constituent of the first coating medium.

20. A cosmetic stick product in accordance with claim 19 wherein the multiple surface coatings on the particles comprise between about 10–75 weight percent of the dry particle weight.

21. A cosmetic stick product in accordance with claim 3 which contains between about 0.05–10 weight percent of a biocidal compound as an additional ingredient.

22. A cosmetic stick product in accordance with claim 3 which contains between about 5–25 weight percent of an antiperspirant compound as an additional ingredient.

23. A cosmetic roll-on product consisting of a liquid organic matrix comprising the following parts by weight of ingredients:

| | |
|---|---|
| volatile oil | 55–70 |
| liquid emollient | 3–10 | and the liquid organic matrix contains between about 0.5–20 weight percent of an encapsulated powder composition homogeneously dispersed therein, wherein the encapsulated powder composition comprises discrete crystallites of at least one ingredient selected from alkali metal and ammonium bicarbonates, which are in the form of particles having a surface coating of a film-forming medium comprising a blend of a polymer and between about 0.1–30 weight percent of a fragrance ingredient, based on the coating weight.

24. A cosmetic roll-on product in accordance with claim 23 wherein the volatile oil ingredient comprises a cyclic or linear polydimethylsiloxane containing 3–9 silicon atoms.

25. A cosmetic roll-on product in accordance with claim 23 wherein the volatile oil ingredient comprises a $C_{12}$–$C_{20}$ branched-chain hydrocarbon.

26. A cosmetic roll-on product in accordance with claim 23 wherein the liquid emollient ingredient is a water-insoluble organic acid, ester or ether compound.

27. A cosmetic roll-on product in accordance with claim 23 wherein the encapsulated bicarbonate crystallites are sodium, potassium or ammonium bicarbonate or any mixture thereof.

28. A cosmetic roll-on product in accordance with claim 23 wherein the fragrance ingredient in the coating is a normally solid organic compound selected from vanillin, ethylvanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, isoeugenol acetate and evernyl, and mixtures thereof.

29. A cosmetic roll-on product in accordance with claim 23 wherein the fragrance ingredient in the coating is a normally liquid organic compound selected from natural or synthetic essential oils, geraniol, eugenol, linalool, citronellol, phenethyl alcohol, methyl ethyl ketone, methylionone and isobornyl acetate, and mixtures thereof.

30. A cosmetic roll-on product in accordance with claim 23 wherein the surface coating on the particles comprises between about 5–70 weight percent of the dry particle weight.

31. A cosmetic roll-on product in accordance with claim 23 wherein the surface-coated particles have a second coating of a film-forming polymer which is the same or different than the polymer constituent of the first coating medium.

32. A cosmetic roll-on product in accordance with claim 31 wherein the multiple surface coatings on the particles comprise between about 10–75 weight percent of the dry particle weight.

33. A cosmetic roll-on product in accordance with claim 23 which has a content between about 0.05–10 weight percent of a biocidal compound as an additional ingredient.

34. A cosmetic roll-on product in accordance with claim 23 which contains between about 5–25 weight percent of an antiperspirant compound as an additional ingredient.

35. A method of practicing personal hygiene which comprises applying a claim 1 cosmetic deodorant product to underarm surfaces in a deodorant-effective amount, wherein the initiation and continuation of deodorizing activity is signaled by a fragrance aroma.

36. A method in accordance with claim 35 wherein the deodorant product is a cosmetic stick or roll-on formulation.

37. An encapsulated bicarbonate salt powder composition comprising discrete crystallites of at least one ingredient selected from alkali metal and ammonium bicarbonates, which are in the form of particles having a surface coating of a film-forming medium comprising a blend of a polymer and between about a 0.1–30 weight percent fragrance ingredient, based on the coating weight.

38. An encapsulated powder composition in accordance with claim 37 wherein the bicarbonate crystallites have an average particle size in the range between about 5–80 microns.

39. An encapsulated powder composition in accordance with claim 37 wherein the encapsulated bicarbonate crystallites are sodium, potassium or ammonium bicarbonate or any mixture thereof.

40. An encapsulated powder composition in accordance with claim 37 wherein the fragrance ingredient in the coating is a normally solid organic compound selected from vanillin, ethylvanillin, coumarin, tonalid, calone, heliotropene, musk xylol, cedrol, musk ketone, benzophenone, raspberry ketone, methyl naphthyl ketone beta, phenyl ethyl salicylate, veltol, maltol, maple lactone, isoeugenol acetate and evernyl, and mixtures thereof.

41. An encapsulated powder composition in accordance with claim 37 wherein the fragrance ingredient in the coating is a normally liquid organic compound selected from natural or synthetic essential oils, geraniol, eugenol, linalool, citronellol, phenethyl alcohol, methyl ethyl ketone, methylionone and isobornyl acetate, and mixtures thereof.

42. An encapsulated powder composition in accordance with claim 37 wherein the surface coating on the particles comprises between about 5–70 weight percent of the dry particle weight.

43. An encapsulated powder composition in accordance with claim 37 wherein the polymer constituent of the surface coating on the particles is a hydrophilic polymer or a water-insoluble polymer or a mixture thereof.

44. An encapsulated powder composition in accordance with claim 37 wherein the polymer constituent of the surface coating on the particles is a polysaccharidic derivative.

45. An encapsulated powder composition in accordance with claim 37 wherein the polymer constituent of the surface coating on the particles is a hydrocolloid.

\* \* \* \* \*